US010517985B2

(12) United States Patent
Knaack et al.

(10) Patent No.: US 10,517,985 B2
(45) Date of Patent: *Dec. 31, 2019

(54) COMPOSITIONS AND METHODS FOR HEMOSTASIS

(71) Applicant: Abyrx, Inc., Irvington, NY (US)

(72) Inventors: David Knaack, Irvington, NY (US);
John Pacifico, Irvington, NY (US);
Marci Wirtz, Irvington, NY (US);
Richard L. Kronenthal, Irvington, NY (US); Frank Do, Irvington, NY (US);
Aniq Darr, Irvington, NY (US)

(73) Assignee: Abyrx, Inc., Irvington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,652

(22) Filed: Aug. 7, 2018

(65) Prior Publication Data
US 2018/0344893 A1 Dec. 6, 2018

Related U.S. Application Data

(63) Continuation of application No. 14/354,188, filed as application No. PCT/US2012/063022 on Nov. 1, 2012, now abandoned.

(60) Provisional application No. 61/554,020, filed on Nov. 1, 2011.

(51) Int. Cl.
| A61L 24/00 | (2006.01) |
| A61L 27/44 | (2006.01) |
| A61L 27/50 | (2006.01) |
| A61L 27/56 | (2006.01) |
| A61L 24/02 | (2006.01) |
| A61L 24/04 | (2006.01) |
| A61L 24/08 | (2006.01) |

(52) U.S. Cl.
CPC ............ *A61L 24/00* (2013.01); *A61L 24/001* (2013.01); *A61L 24/0089* (2013.01); *A61L 24/02* (2013.01); *A61L 24/046* (2013.01); *A61L 24/08* (2013.01); *A61L 27/446* (2013.01); *A61L 27/50* (2013.01); *A61L 27/56* (2013.01); *A61L 2400/04* (2013.01)

(58) Field of Classification Search
None
See application file for complete search history.

(56) References Cited

U.S. PATENT DOCUMENTS

| 2,642,375 | A | 6/1953 | Henderson et al. |
| 2,772,999 | A | 12/1956 | Masci |
| 4,439,420 | A | 3/1984 | Mattei et al. |
| 4,440,789 | A | 4/1984 | Mattei et al. |
| 4,568,536 | A | 2/1986 | Kronenthal et al. |
| 5,356,629 | A | 10/1994 | Sander et al. |
| 5,696,101 | A | 12/1997 | Wu et al. |
| 6,056,970 | A | 5/2000 | Greenawalt et al. |
| 6,060,461 | A | 5/2000 | Drake |
| 6,214,808 | B1* | 4/2001 | Soe ..................... A61K 31/717 514/57 |
| 6,420,454 | B1 | 7/2002 | Wenz et al. |
| 6,923,961 | B2 | 8/2005 | Liu et al. |
| 7,074,425 | B2 | 7/2006 | Constantine et al. |
| 7,553,913 | B2 | 6/2009 | Wellisz et al. |
| 7,829,616 | B2 | 11/2010 | Wellisz et al. |
| 7,914,819 | B1 | 3/2011 | Wen et al. |
| 7,989,000 | B2 | 8/2011 | Kronenthal |
| 2002/0010150 | A1 | 1/2002 | Cortese et al. |
| 2005/0065214 | A1* | 3/2005 | Kronenthal ............ A61K 31/19 514/557 |
| 2006/0013857 | A1* | 1/2006 | Kronenthal ............ A61K 31/19 424/426 |
| 2009/0005716 | A1* | 1/2009 | Abuzaina ............... A61L 24/001 602/43 |
| 2009/0062233 | A1 | 3/2009 | Ji et al. |
| 2009/0186851 | A1 | 7/2009 | Hardy et al. |
| 2009/0254194 | A1 | 10/2009 | Peters et al. |
| 2009/0286886 | A1 | 11/2009 | Fisher et al. |
| 2012/0258159 | A1 | 10/2012 | Vogt |
| 2014/0275287 | A1 | 9/2014 | Knaack et al. |
| 2018/0361014 | A1 | 12/2018 | Knaack et al. |

FOREIGN PATENT DOCUMENTS

| EP | 1 829 564 A1 | 9/2007 |
| EP | 2 508 210 A2 | 10/2012 |
| GB | 725887 A | 3/1995 |

OTHER PUBLICATIONS

Anonymous: "Bone wax", Wikipedia, Feb. 7, 2018.
Das J M: "Bone Wax in Neurosurgery: A Review", World Neurosurgery, vol. 116, Jan. 1, 2018 (Jan. 1, 2018), pp. 72-76.
Geary J et al.: "New absorbable hemostatic bone wax", Annals of Surgery, Dec. 1, 1950 (Dec. 1, 1950), pp. 1128-1137.
International Search Report of PCT/US2012/063022, dated Feb. 27, 2013.
Supplementary European Search Report issued for EP 12 84 5696 completed on Oct. 21, 2015 and dated Oct. 29, 2015.
Synthes Usa Products: "Synthes Hemostatic Bone Putty",, Apr. 20, 2011 (Apr. 20, 2011), pp. 1-5.
Wang M et al.: "A New, Pluronic-based, Bone Hemostatic Agent That Does Not Impair Osteogenesis", Neurosurg, vol. 49, No. 4 Oct. 1, 2001 (Oct. 1, 2001), pp. 962-968.
Wellisz T: "Management of Bone Bleeding During Surgery and Its Impact on the Incidence of Post-Operative Osteomyelitis",Osteomyelitis, Mar. 1, 2012 (Mar. 1, 2012), pp. 153-180.
Wellisz T et al.: "Ostene, a New Water-Soluble Bone Hemostasis Agent", The Journal of Craniofacial Surgery, vol. 17, No. 3, May 1, 2006 (May 1, 2006), pp. 420-425.
The United States Pharmacopeial Convention. "General Notices and Requirements, Applying to Standards, Tests, Assays, and Other Specifications of the United States Pharmacopeia," USP 34, (2010): p. 6.

* cited by examiner

Primary Examiner — Jared Barsky
(74) Attorney, Agent, or Firm — Cooley LLP; Ivor R. Elrifi; Matthew Pavao

(57) ABSTRACT

The present invention relates to water soluble and completely absorbable and/or physiologically degradable hemostatic compositions having a wax or wax-like base effective for tamponade hemostasis of bone or cartilage.

8 Claims, 6 Drawing Sheets

COMPOSITIONS AND METHODS FOR HEMOSTASIS

RELATED APPLICATIONS

This application is a continuation of U.S. application Ser. No. 14/354,188, which is a national phase filing under 35 USC § 371 of International PCT Application for PCT/US2012/063022, filed on Nov. 1, 2012, which claims the benefit of U.S. Provisional Application No. 61/554,020, filed on Nov. 1, 2011, each of which is incorporated by reference herein in its entirety.

FIELD OF THE INVENTION

The present invention relates to compositions for use in medical and surgical procedures to control tissue bleeding from dense tissues such as bone or cartilage, and, in particular, as hemostatic tamponades.

BACKGROUND OF THE INVENTION

A number of different base materials have been described for the manufacture of compositions intended to achieve hemostasis on bleeding tissue. Many of these are suitable for soft tissues. For example, U.S. Pat. No. 6,060,461 describes porous particles of a polysaccharide, preferably cross-linked dextran, to promote blood clotting on soft tissue. The particles, as described, are "designed to act as a sieve to dehydrate the blood and accelerate the natural blood clotting process," US 2009/0062233 describes a hemostat in powder form based on modified starch. U.S. Pat. No. 6,056,970 describes a polysaccharide-based matrix combined with a fibrin glue or a collagen patch containing, e.g., aprotinin, fibrinogen, and/or thrombin. U.S. Pat. No. 6,923,961 describes hemostatic compositions of derivatized CMC/polyethylene oxide (PEO) composites containing chemical hemostatic agents such as thrombin.

For use in bone, a hemostatic tamponade must adhere to the hard, moist surface of bleeding bone or cartilage while not adhering appreciably to surgical gloves and instruments. The composition must also be sufficiently moldable for easy application to the site. Optimal formulations are able to withstand the force of saline irrigation that accompanies typical surgical procedures. The durability of the composition in the in vivo environment should be sufficient for the composition to serve as an effective hemostatic tamponade at the wound site throughout the entire intraoperative period and for a sufficient time after surgery to ensure bleeding has stopped. The term "tamponade" refers to the mechanical hemostasis occurring when a material is applied to a bleeding surface to occlude the vessels or pores through which blood flows, creating a static interface between the material and the dammed blood flow. Normal clotting can then occur within this static interface. Compositions unsuitable for use as a tamponade do not adhere directly to the bleeding are easily dislodged by the force of flowing blood or surgical irrigation, or are too water-soluble.

The traditional and still widely used composition for tampanade hemostasis of hone or cartilage is bone wax. Bone wax is generally made from beeswax and a softening agent such as iospropyl palmitate. Its main disadvantage is that it is nondegradable and nonabsorbable under physiological conditions. This results in undesirable effects such as inhibition of bone healing and osteogenesis and, as with any nonabsorbable foreign body implant, promoting infection, inflammation, and pain.

Several absorbable or partially absorbable alternatives to traditional bone waxes have been described. For example, U.S. Pat. No. 4,568,536, by Kronenthal, et al., and U.S. Pat. No. 4,439,420 by Mattei, et al., describe compositions featuring particulate solid materials suspended in oils and highly water soluble solid poloxamers (ie Pluronics). U.S. Pat. No. 7,989,000 by Kronenthal describes compositions containing a solid particulate fatty acid salt suspended in a liquid poloxamer along with certain other excipients. U.S. Pat. No. 5,356,629 by Sander, et al., describes a composition containing coated particles of polymethylmethacrylate in a matrix of cellulose ether, collagen, or hyaluronic acid. U.S. Pat. Nos. 7,553,913 and 7,829,616 by Weilisz, et al., describe hydrophilic water soluble waxy compositions comprising a base of a random copolymer comprising ethylene oxide and one or more other alkylene oxide(s) which may be mixed with solid particles. U.S. Pat. No. 7,914,819 by Wen, et al., describes a polymeric matrix having a polysaccharide backbone. U.S. Pat. No. 7,074,425 by Constantine, et al., describes hydrophilic polyethylene glycol based compositions consisting of fixture of a high and a low molecular weight polyethylene glycol of HLB (hydrophilic lipophilic balance) greater than 20.

Despite the progress that has been made in this field, there remains a need for an alternative to "bone wax" that is as effective in achieving tamponade hemostasis for a suitable time while also being completely biodegradable or absorbable. Water-soluble wax-like compositions described by e.g., Wellisz (including the commercially available OSTENE) suffer from the disadvantage of not being durable under surgical conditions to maintain adequate hemostasis for a sufficient period of time. See, e.g., Holman, 2007. With the exception of traditional hone wax, water-insoluble waxes have not generally been utilized in the preparation of hemostatic tamponades because of their insolubility in the aqueous in vivo environment and their inability to be phagocytized.

The present invention overcomes these disadvantages by providing compositions based upon water-soluble wax-like substances that are formulated to maximize their durability under surgical conditions while maintaining optimal absorbability and/or degradability under physiological conditions.

SUMMARY OF THE INVENTION

The present invention provides a hemostatic composition of putty-like consistency effective for tamponade hemostasis of bone or cartilage comprising a freely water soluble (FWS) non-particulate solid base material and a dissolution retardant or a dispersion accelerant, wherein the time to complete dissolution or dispersion of the composition in vitro is at least 10 times greater than a reference formulation that consists of PEG 1450/PEG 400 90%/10% by weight.

In some embodiments the FWS non-particulate solid base material surfactant having an HLB less than 20.

In additional embodiments the FWS non-particulate solid base material may be a surfactant having a molecular weight of at least 4000 kilodaltons (kD), and may further comprise a softener.

In some embodiments, the invention may further comprise a microporous particulate ceramic material embedded within solid base material and a rapidly hydrating polysaccharide.

In additional embodiments, the macroporous particulate ceramic material of the current invention may be present in an amount that may be less than about 60% by weight of the putty and the polysaccharide may be present in an amount that is up to 15% by weight of the putty.

In some embodiments, the invention may further comprise polypropylene oxide.

The invention further provides a hemostatic composition, which may comprise an absorbent particulate, wherein when the composition may be exposed to water the rate of water absorption in the first hour may be equal to or exceeds the dissolution of the solid surfactant.

In some embodiments, the invention may further comprise a water absorbing dissolution retardant.

In one embodiment, provides a hemostatic composition of putty-like consistency effective tamponade hemostasis of bone or cartilage, which comprises a poorly water soluble (PWS) non-particulate solid base material and a dispersion accelerant, where the PWS base material may be a water insoluble wax-like material.

In one embodiment, the invention provides bone substitute composition, which comprises a rounded, microporous, particulate ceramic suspended in a non-particulate water soluble base.

In some embodiments the bone substitute is a hand moldable bone substitute comprising a solid surfactant and less than 70% by weight of a biphasic microporous calcium phosphate in the form of rounded granules wherein said granules have a density greater than 2.5.

BRIEF DESCRIPTION OF THE FIGURES

FIG. 5A shows a bar graph of the effect of time on the dissolution or water uptake and the percentage of mass. FIG. 5B shows a bar graph on the effect of time on the dissolution or water uptake on the percentage rate.

DETAILED DESCRIPTION OF TUE INVENTION

Figure 1A:
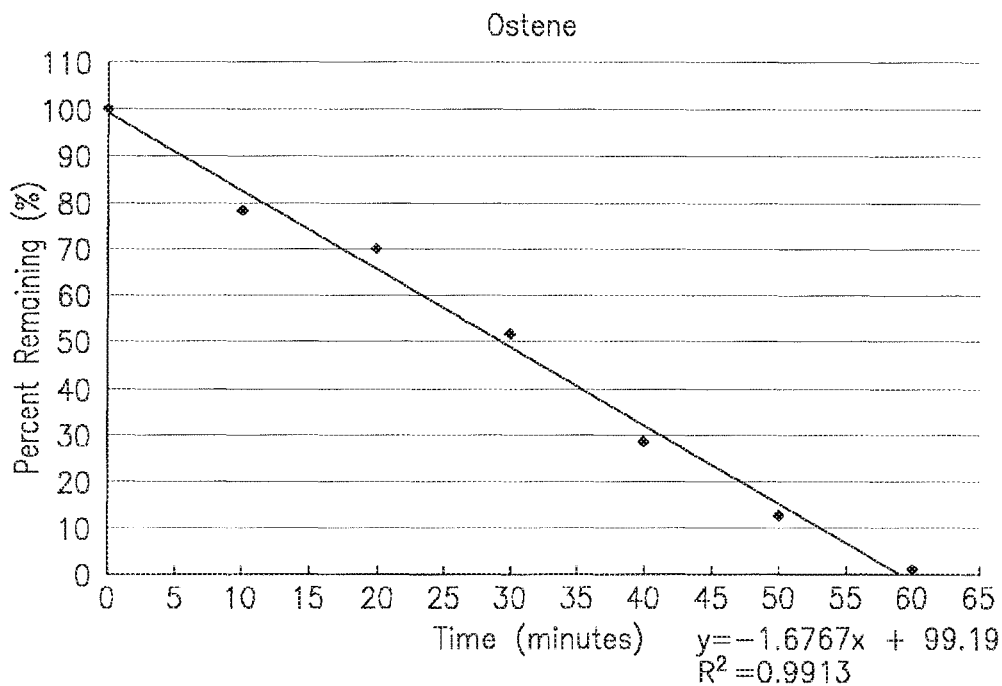
FIGS. 1A-B: Graphs of the dissolution kinetics of two compositions derived using the biopsy bag method (see specification for details). (A) OSTENE, a mixture of water-soluble alkylene oxide block copolymers (derived from ethylene oxide and propylene oxide) and a random copolymer of polyethylene and polypropylene glycols undergoes complete dissolution in about 105 minutes at 37° C. (B) PEG 1450/400 ("PEG reference formulation"), a mixture of polyethylene glycols of different molecular weights undergoes complete dissolution in less than 10 minutes.

The compositions of the invention control blood loss from bleeding tissue including hone or cartilage surfaces and, optionally, provide a means for the controlled release of one or more therapeutic agents and support of hone and tissue growth at the site of application. In certain embodiments, the compositions of the invention also serve to fill a void or gap in bone or cartilage. The compositions of the invention are superior to certain other bone waxes in their enhanced durability under surgical conditions as evidenced by their ability to maintain tamponade hemostasis at the site of application for at least 3 hours and preferably for at least about 6 or at least about 8 hours.

The compositions of the invention are formed from a mixture comprising non-particulate solid that is either freely water soluble (FWS) or poorly water-soluble/insoluble (PWS). The FWS and PWS non-particulate solids (formulation bases) used to form the compositions of the invention are generally wax or wax-like solids under ambient conditions. The term "wax", as used herein, refers to both water-soluble and water-insoluble waxes and wax-like solids. A wax, according to the invention, is a solid at room temperature and generally has a melting point above 30° C., preferably above 40° C., and most preferred above 45° C. Water-soluble waxes suitable for use in the compositions of the invention include, for example, water soluble poly (oxiranes), or poly(alkylene oxides), water-soluble esters of fatty acids (such as phospholipids), and ethoxylated fatty acids (such as PEG stearates and Poloxamer stearates). Thus, a wax-like solid in this context, is physically, but not necessarily chemically, similar to a traditional wax (a solid ester of a fatty acid and a fatty alcohol) or a solid paraffin of suitable molecular weight.

The compositions of the invention are able to maintain tamponade hemostasis at the site of application for suitable periods of time. The invention provides in vitro methods for screening the inventive compositions relative to formulations already existing in the art. For FWS compositions, these screening methods allow the identification of formulations that dissolve more slowly than previous formulations of the art, and the development of new formulations with better intraoperative hemostatic reliability, with less rebleeding than observed with the existing compositions of the art. For PWS formulations, which are expected to have excellent intraoperative hemostatic reliability, the in vitro assays allow the determination of appropriately active dispersion accelerators. Preferably, the compositions of the invention are able to maintain hemostasis in such an assay for at least 15 minutes, at least 30 minutes, at least 90 minutes, at least 120 minutes, or for from about 30 to 60 minutes or 60 to 120 minutes, 90 to 120 minutes, 120 to 180 minutes, 180 to 240 minutes, or longer.

In certain embodiments, the compositions of the invention are able to maintain tamponade hemostasis intraoperatively and postoperatively at the site of application for periods of time including 1.5 to 3 hours, 3 to 6 hours, 6 to 9 hours, or 9 to 12 hours without appreciable re-bleeding or the need for reapplication of the material. In certain embodiments, the hemostasis efficacy of the compositions is measured with an in vivo assay, for example, using living rabbit hone as described herein.

Following implantation in the body, the compositions of the invention are eliminated from, absorbed or degraded in, the body in up to about 1 to 2 weeks. In other embodiments, the compositions are absorbed, eliminated, or degraded in about 12 hours, 24 hours, or 48 hours.

In certain embodiments, after implantation in vivo, the inventive compositions absorb and/or disperse from the implant site in less than 7 days, preferably less than 4 days and many compositions will substantially absorb in less than 192, 120, 96, 72, 48 or 24 hours. The most preferred compositions will be effective at maintaining intraoperative hemostasis without the need for reapplication for 6 hours or more and will be substantially resorbed or dispersed within 96 hours after implantation.

In some embodiments, particulate solids are included to provide or enhance specific performance characteristics of the formulations. Added particles may be absorbable, non-absorbable, or resorbable, or mixtures of particles with a variety of properties may be included according to need. Particles may be introduced to affect overall dispersion, or elimination of the formulation from the implant site following implantation. Particles may be added to affect the handling, stiffness, flowability, osteoconductivity, or water resistance of the formulation. Other examples of additives or fillers or whiskers to provide additional putty coherence or improve other mechanical properties of the compositions include poly ether ether ketone (PEEK), REPLACE (Cortek, Inc.), EXPANCEL (Akzo Nobel), natural fibrous materials including proteins, polysaccharides, extracellular matrix components, absorbable silks, collagen, fibrin, fibrinogen, thrombin, and absorbable polymers including polylactides, polycaprolactones, polyglycolides, polyurethanes and derivatives and combinations or copolymers thereof. In other embodiments, the particulate material is a ceramic such as substituted calcium phosphates (e.g, silica, strontium, or magnesium salt substitution) or a glass such as bioglass or absorbable phosphate glass. In some embodiments, the particulate material is one or more of calcium sulfate, calcium phosphosilicate, sodium phosphate, and calcium aluminate. The optional particulate material, when present, may comprise any one or more of the materials listed in the embodiments above.

In certain embodiments, the compositions of the invention do not contain added water. In one embodiment, a composition of the invention is anhydrous.

In one embodiment, the compositions of the invention do not contain an active chemical hemostatic agent.

In one embodiment, the compositions do not contain dextran, alginate, modified starch, or chitosan.

In one embodiment, the compositions do not contain microfibrillar collagen.

In one embodiment, the compositions of the invention do not contain a hydrogel forming material such as sodium carboxymethylcellulose.

In one embodiment, the compositions do not contain a thermosetting material.

In certain embodiments, the compositions of the invention do not require pre-preparation by the application of heat and instead are hand moldable and formable at room temperature.

Preferably, the compositions have a low degree of tackiness and are compatible with surgical gloves. That is, the compositions do not adhere appreciably to latex or nitrile surgical gloves or similar materials. At the same time, the compositions of the invention have sufficient tack strength to adhere to the moist surfaces of bleeding bone or cartilage.

The compositions are often formed from a process that includes melting the combined liquid and solid components into a single homogenous liquid that is then allowed to solidify. Continuous mixing may be applied during the cooling phase to prevent phase separation, when appropriate. Prior to full cooling, the formulations may be introduced into a mold or an extrusion apparatus and may be molded into specific shapes or extruded before or after cooling, depending upon the temperature dependence of the viscosity of the specific formulation.

FWS-Based Compositions

The compositions of the invention may employ more slowly dissolving FWS non-particulate bases than described in the art, or otherwise utilize a dissolution retardant to slow the dissolution rate. In general, at least about 50% by weight of the (particle-free portion) composition is the FWS base. Suitable FWS base materials include moderately hydrophobic materials which absorb more slowly than existing formulations (e.g., than Ostene), may be prepared from moderately hydrophobic solid wax-like materials such as surfactants with HLB values of less than 20, or less than 17, or HLB values of 15 or less. Such surfactants are available commercially, for example under the trade names BRIJ, MYRJ, AMITER, CREMOPHOR, and LIPOSORB.

Other FWS base materials include polyethylene glycols of 4,000 kD molecular weight and higher. Compositions of the present invention comprising such PEG base materials have a 5 to 30-fold dissolution times than that a reference composition (see FIG. 1).

Chemically, suitable FWS base materials include any soluble waxes such as biocompatible poly(oxiranes) (or poly(alkylene oxides)), block and/or random polymers or copolymers of ethylene and propylene glycol and polypropylene glycol, and their fatty acid ester or ether derivatives. Exemplary polyoxiranes include polyoxirane alcohols, polyoxirane esters (mono, di and poly), polyoxirane ethers (mon, di and poly) and polyoxirane alkanes. Further non limiting examples of suitable FWS base materials include water soluble surfactants having HLB values greater than 3, 5 or 7, and preferably greater than 10 or 15, but the most useful base materials have HLBs less than 20. Non-limiting examples include soluble ethoxylated fatty acids including fatty acid substituted polyethylene glycols (PEGs) such as PEG stearate ester, e.g., POLYOXYL 40 Stearate (Myrj® 52 (40) Monostearate,), polyethylene glycols (PEGs), substituted PEGS, polyethylene glycol laurate, derivatized block copolymers based on ethylene oxide and propylene oxide (e.g., poloxamers or PLURONICs), soluble sorbitan derivatives, and phospholipids.

Figure 3:
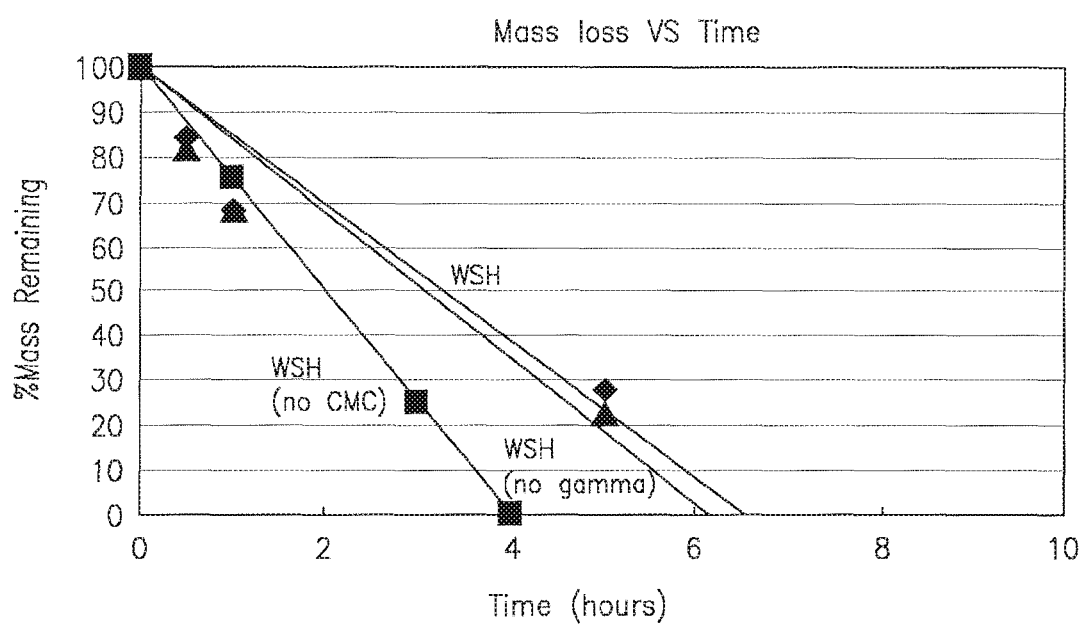
FIG. 3: Dissolution kinetics of representative inventive compositions. Samples were prepared as described for FIG. 2. Dissolution kinetics were determined by the mesh basket method (see specification for method details).
Figure 4:
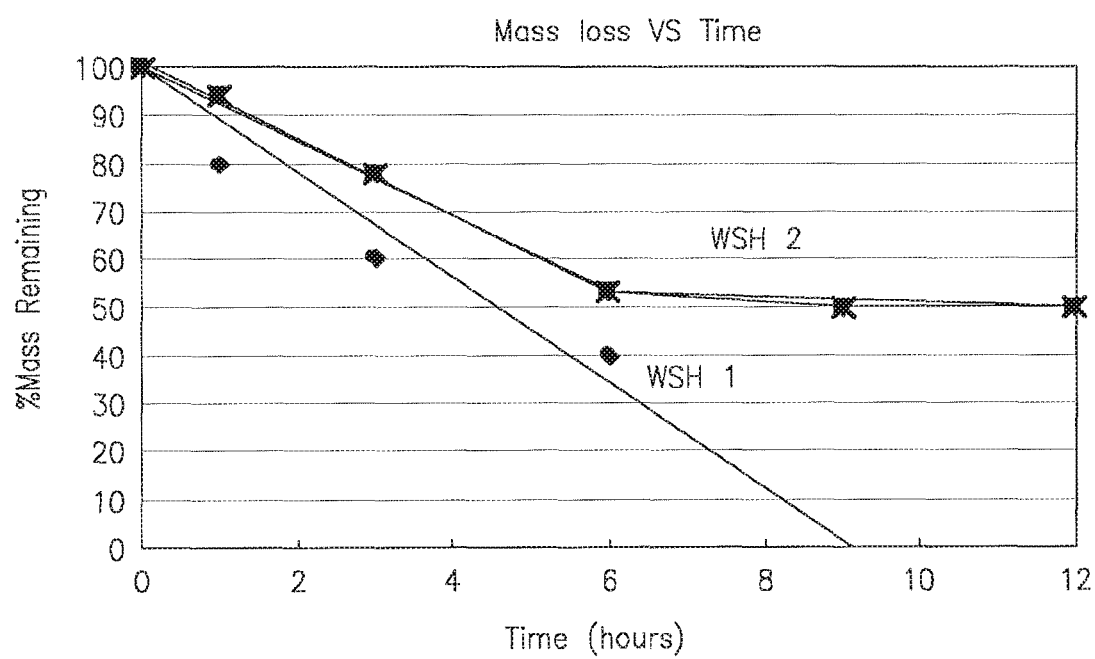
FIG. 4: Dissolution kinetics of representative inventive compositions. Samples were prepared as described in FIG. 2. Dissolution kinetics were determined by the mesh basket method (see specification for method details).
Figure 5A:
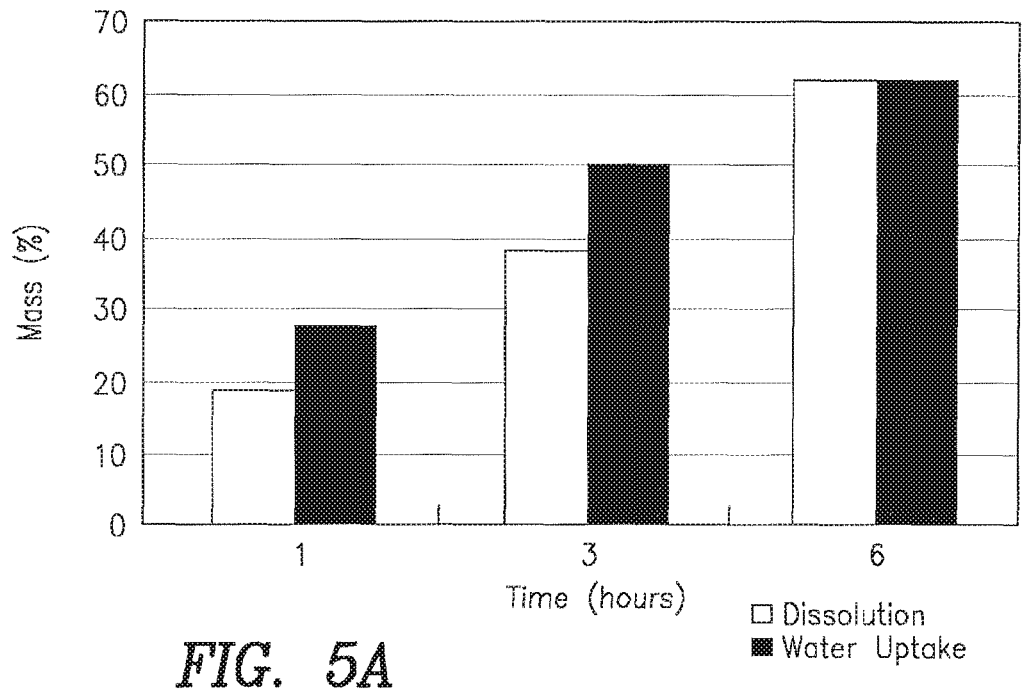
FIGS. 5A-B.
Figure 5B:
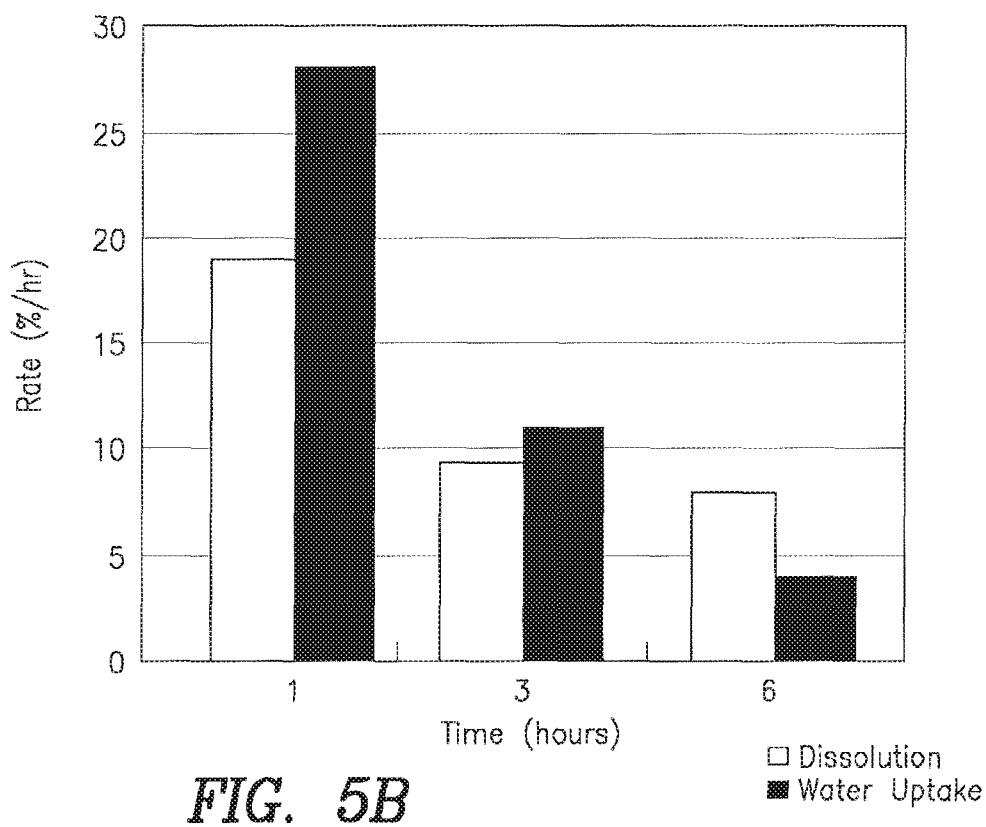
Figure 6:
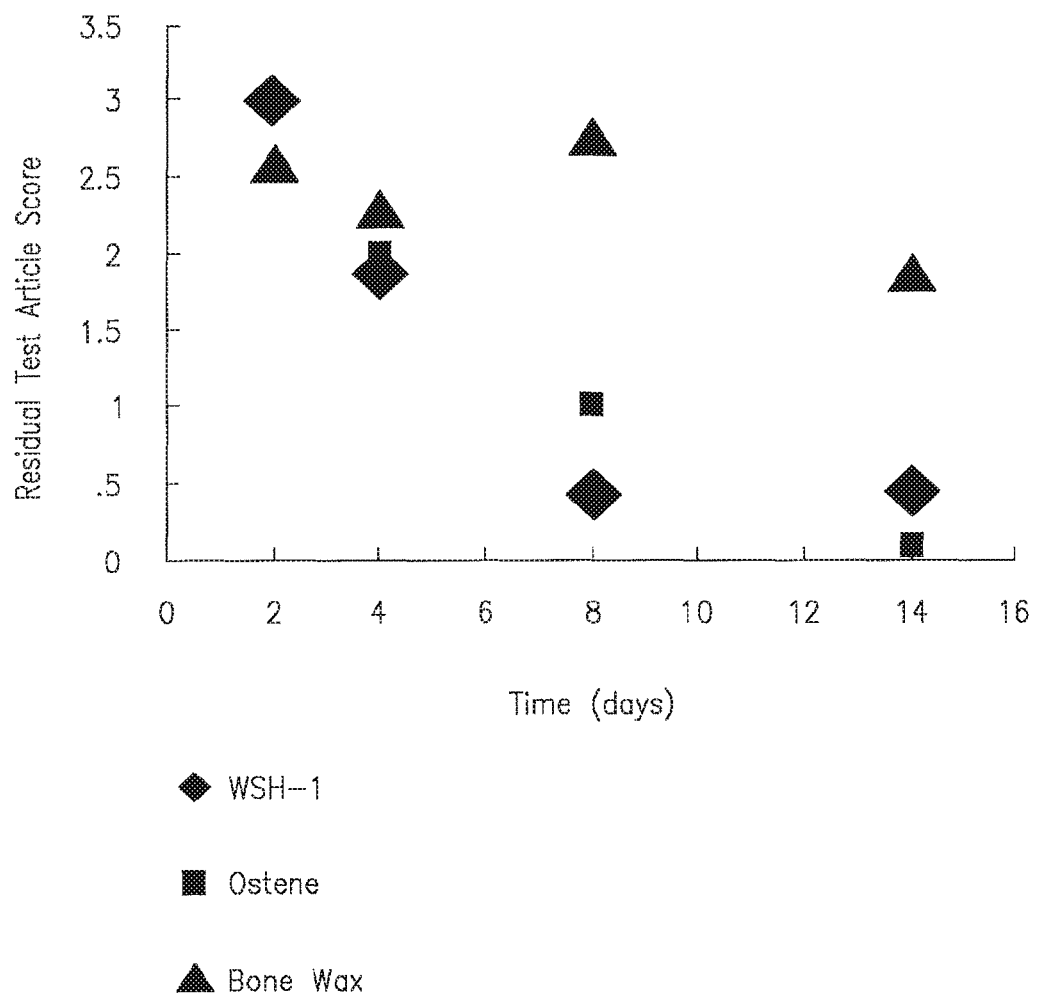
FIG. 6: In vivo absorption time of the inventive compositions compared to controls. Product implanted in 3 mm holes in the rabbit femur.

For those non-particulate FWS solid bases for which dissolution occurs more rapidly (e.g., low molecular weight surfactants with HLBs greater than 15 or 20) than desired, dissolution retardants may be employed. A typical class of dissolution retardant is the rapidly hydrating polysaccharides. Sodium carboxymethyl cellulose (CMC) is a member of this class. Incorporation (by mixing) of 23% dry CMC powder by weight into a commercially available product, Ostene, increased its dissolution time in the beaker assay by over four fold (see Example 1a & b). Similarly, incorporation of 9.1% CMC into a PEG-based reference composition (PEG1450/400—see formula 2a) increased dissolution time approximately 15-fold. Additional examples of dissolution retardation after the incorporation of CMC are provided in examples 1, 2, 3, 5, 11, and FIG. 3.

The dissolution retardant is present at less than about 50% by weight of the composition. A retardant (e.g. a liquid surfactant) suitable for use with a particular base is one that forms a homogenous mixture with the base and does not phase separate. Hydrogel-forming retardants are generally an exception to this principle and are usually included in the formulations in a dry powder form suspended within the formulation. Preferably, the retardant dissolves more slowly than the FWS base. In one embodiment, the retardant is a rapidly hydrating hydrogel forming material. Suitable gel forming materials include, for example, gel-forming poloxamers (including thermosetting and phase transitioning poloxamers), hydroxypropylmethylcellulose, chitosan hydrochloride, sodium carboxymethylcellulose, sodium polyacrylic acid, and sodium polymethacrylic acid, and polysaccharide glycolates such as the starch glycolates including the sodium salt. When hydrogel-forming materials are incorporated as the dissolution retardant, gel formation should occur rapidly, i.e., the molecules must readily undergo hydration and gelation prior to full solubilization of the primary component. During the first hour of dissolution, it is preferred that the rate of mass loss of the FWS components (as opposed to the hydrogel) relative to the starting weight of the dry formulation, does not exceed the rate of water uptake by the overall formulation (relative to formulation starting weight). In general, the water uptake rate over the first hour is from 75% to greater than 200% of the dissolution rate (measured dry) of the soluble components. In preferred embodiments, water uptake rate is 100%, 125%, 150%, or greater than the dissolution rate. The rate of water uptake during the first half hour should also exceed the dissolution rate.

Slow-to-hydrate molecules generally do not form gels prior to significant diffusion of the soluble material and therefore cannot impact the overall dissolution rate of the formulation. Examples of materials that hydrate at an inadequate rate include: sodium alginate, collagen, gelatin, and oxidized cellulose. Hydration inducing mechanisms such as reduction of particle size and partially pre-hydrated gel-forming materials, and/or pretreatment of the gel forming particles with a surfactant may be employed to encourage early hydration in these and similar molecules. Examples of materials which hydrate over a sufficiently rapid time course to effectively modulate dissolution of the primary soluble component include: substituted polysaccharides, sodium carboxymethylcellulose (low, medium and high viscosities, e.g., from Sigma Life Sciences), starch glycolates, and chitosan hydrochloride.

For in vitro screening of dissolution properties under the conditions described herein, a suitable time for complete dissolution in a buffer at 37° centigrade is at least 60 minutes, or from 60 to 90 minutes, 70 to 100 minutes, from 90 minutes to 120 minutes, from 2 to 4 hours, from 4 to 6 hours, or from 6 to 8 hours. Dissolution time may also be expressed relative to the "PEG reference formulation" (PEG 1450/400; see formula 2a). This allows direct comparison of dissolution rates independent of the in vitro dissolution method in use. Preferred compositions will require at least 2.5-fold more time for complete dissolution than the PEG reference formulation. More preferably, the inventive compositions will require 3-fold, 5-fold, or greater than 10-fold the amount of time required for complete dissolution compared to the PEG reference formulation. Many embodiments require 12 to 15-fold or more time to dissolve in the in vitro assay compared to the PEG reference formulation.

Those inventive compositions which comprise sufficiently rapidly hydrating materials may, upon exposure to an electrically conductive aqueous medium (e.g., saline or bodily fluids), be able to conduct an electric charge. Consequently, such formulations, when placed in vivo and exposed to the current produced by electrocautery, in some cases may be prone to sparking or ignition. The inventors have found that limiting the dry hydrogel forming material to less than 20% of the total formulation rate largely eliminates this effect. In order to minimize this possibility, the preferred compositions will generally contain less than about 35%, 30%, 20% or less than 15% of a rapidly hydrating hydrogel forming material. In one preferred embodiment, the formulation comprises from 25-99% of a non-particulate FWS solid base with an HLB of less than 20 and 0.5-15% of a dry, particulate rapidly hydrating polysaccharide (e.g., carboxymethyl cellulose) and is not susceptible to ignition or sparking within the composition when exposed to electrocautery in the presence of saline solution.

Further non-limiting examples of suitable dissolution retardants include poorly water soluble liquids, chemical binders, emollients, detergent builders, and suspending agents. Suitable poorly water soluble liquids include liquid PLURONICs (block copolymers based on ethylene oxide and propylene oxide, also referred to generically as "poloxamers") having an HLB less than 10, liquid glycerol fatty acid esters (e.g., glycerol mono caprylate, and glycerol monocaprate), isocetyl alcohol, Eastman SAIB, and liquid tocopherols including tocopherol acetate. Polypropylene oxide is an insoluble alkylene, oxide polymer that has been found to advantageously reduce dissolution and promote water resistance of some of the inventive compositions utilizing alkylene oxide-based polymers as the FWS, non-particulate base. Non-limiting examples of suitable binders include cellulose esters and hydrogel forming polymers such as hydroxylethyl cellulose, carboxymethyl cellulose (e.g., sodium, potassium, and lithium salts; commercially available FINNEIX from CP Kelco), hydroxypropylmethylcellulose hypromellose, USP), and sodium alginate. Non-limiting examples of emollients include octyl palmitate, microcrystalline cellulose (AVICEL PH). Non-limiting examples of detergent builders include low molecular weight polyacrylic acids, sodium polyacrylate, and salts of poly aspartic acid and poly glutamic acids. Non-limiting examples of suspending agents include sodium polyacrylic acid (CARBOPOL).

In certain embodiments, the FWS-base comprises at least 50 wt % of the non-particulate portion of the composition with the remaining weight comprising one or more dissolution retardants and one or more optional particulates. In one embodiment, the one or more particulates is an osteoconductive material selected from bone or a bone substitute, calcium phosphate; tricalcium phosphate (e.g., alpha or beta tricalcium phosphate), tetracalcium phosphate; dicalcium phosphate; poorly crystalline hydroxyapatite, substituted calcium phosphates (e.g., with magnesium, strontium, or silica salts): calcium pyrophosphate, hydroxyapatite, biphasic calcium phosphates, hydroxyapatite and TCP containing calcium phosphates, multiphasic calcium phosphates, and glasses—both silicate and phosphate based, highly porous nanocrystalline hydroxyapatite (HA) in the presence of nanoporous silica ($SiO_2$) in a sol-gel combination; glass-ionomer, absorbable phosphate glass, calcium sulfate, an osteoconductive plastic (e.g. tyrosine polycarbonates or tyrosine polyarylates and derivatives), polymer or polyurethane, or any combination thereof.

In one embodiment, the composition comprises an osteoconductive material in particulate form in an amount of from about 5 to 70% (wt/wt), 5 to 50%, 20 to 30%, or 1 to 20% of the final composition. In one embodiment, the one or more osteoconductive materials are in the form of a particle, a fiber, or a whisker with minimal cross-sectional diameters ranging from 0.00001-100 mm. In a preferred embodiment the average particle diameter is between 100 to 750 microns. In a more preferred embodiment the particles are rounded and microporous. In another embodiment, the particulate ceramic comprises less than 75%, less than 50%, less than 40%, 35%, less than 30% or less than 20% of the total volume of the composition.

In one preferred embodiment of the invention the formulation comprises particles embedded within a putty-like soft, solid wax (e.g., a surfactant) base. The presence of the particles provides a.) frictional resistance to facilitate purchase of the formulation of the putty against the surface of bone, and improve retention of the putty at the implant site, b.) improved handling and putty stiffness, and optionally, c.) radiopacity to the formulation. In more preferred aspects of this embodiment, the particles are rounded or spherical to further optimize moldability and spreadability at the implant site (compared to irregular particles which create resistance to moldability and spreadability) while still improving frictional resistance compared to the absence of particles. In still more preferred embodiments, the rounded particles comprise a microporous ceramic (e.g., glass, bioglass, calcium phosphate and/or calcium carbonate, and their derivatives), having average pore size of less than 1000 microns, less than 75, 50, 25, 10, 5 or less than one micron. In other preferred embodiments, the rounded microporous particles comprise a biphasic calcium phosphate (e.g. HA/TCP with weight % ratio of hydroxyapatite of 5, 15, 25, 40, 50 or 60%) and have a density of 0.7, 1, 1.5, 2, 2.5, 3, or greater than 3 gm/cc. Finally, the invention contemplates a bone void filler with or without hemostatic properties (e.g. a hemostatic bone substitute) comprising a non-particulate water soluble surfactant with an HLB of less than 20 (eg, polyoxyethylene 40 stearate) and further comprising rounded microporous ceramic particles of 15-55% by weight, where in the particles have a bulk density greater than 2.5 gm/cc.

PWS-Based Compositions

The compositions of the invention having a non-particulate PWS base require a dispersion accelerant that may be non-particulate or particulate. As used herein "non-particulate PWS base" means the PWS material is either sourced as a monolithic wax or was prepared from a melt of a particulate base. In certain embodiments, the composition is formed from one or more PWS bases and/or one or more accelerants.

In accordance with this embodiment, at least about 50% by weight of composition is the PWS base. Suitable PWS base materials include mono-, di-, or tri-fatty acid esters such as glycerol and sorbitan mono fatty acid esters (stearates, palmitates, laurates), and cholesterols. Other suitable insoluble and poorly soluble waxes are known to the art and are cataloged in McCutheon's (2009) (volumes 1 & 2 Manufacturing Confectioner Publishing Co. Princeton, Wis.).

The dispersion accelerant is present at less than 50% by weight of the composition. Preferably, the accelerant is present in an amount that is about 1.0 to 20% or 1 to 10% by weight of the composition. A suitable accelerant for use with a particular base is one that forms a homogenous mixture with the base. Accelerants generally serve to disperse or solubilize the base within an aqueous environment. When an insoluble stearate wax is used, preferred accelerants include soluble stearates such as PEG stearate, liquid glycerol fatty acid monoesters, low HLB liquid surfactants (e.g., <20).

In one embodiment, particles are used to promote the aqueous dispersion of the PWS base. In accordance with this embodiment, the particles are generally hydrophilic, poorly soluble in water, and metabolizable (e.g., biocompatible ceramics, calcium phosphate, hydroxyapatite, tricalcium phosphate, bioglass, demineralized bone, mineralized cancellous or cortical bone, lyophilized protein, allograft, xenograft, and/or autogenous bone). In some cases the particles are freely soluble in water soluble, biocompatible salts of calcium phosphate, sugars, salts, polysaccharides, hydrogels formers and/or precursors, etc.). Particulate dispersants may be in granular or powder form, micron or submicron in size. In this context, the size refers to the size of the particle in its largest dimension and is generally given as a mean average particle size. Preferably, the particles are 1000 microns or less in size. In certain embodiments the particles are 750 microns or less, 500 microns or less, 250 microns or less, or 100 microns or less in size. When submicron particles are used as accelerants, their particle size can range from 0.1 to 1, 5, 10, or 50 microns.

In other embodiments, hydrotropic coupling agents are preferred accelerants. These include glyceryl caprate or caprylate (Capmul, Captex, etc) or organic phosphate derivatives such as lecithin and water-based organofunctional silanes. Some preferred accelerants have an affinity for the PWS (e.g., PEG stearate and glycerol monostearate).

In certain embodiments, the PWS-based composition comprises at least about 50% of the PWS base, one or more dispersion accelerants and one or more particulates. In one embodiment, the one or more particulates is an osteoconductive material selected from the same list of materials previously described for FWS formulations. In one embodiment, the composition comprises an osteoconductive material in an amount of front about 5 to 50% (wt/wt), 5 to 40%, 20 to 30%, or 1 to 20% of the final composition. In one embodiment, the one or more osteoconductive materials are in the form of a particle, a fiber, or a whisker with minimal cross-sectional diameters ranging from 0.00001-1.00 mm. Considerations for included particulates in the PWS formulations are the same as with FWS compositions.

Therapeutic Agents

The compositions of the invention may optionally include one or more therapeutic agents. In various embodiments, the therapeutic agents are added to the compositions of the invention in solid form, either directly to the melted mixture of components when the therapeutic agent is heat stable, or during or after solidification by mixing or blending. The one or more therapeutic agents may be any suitable or desirable therapeutic agent known to the skilled artisan. In a specific embodiment, a composition of the invention optionally comprises one or more of an antimicrobial, a local anesthetic or analgesic, an anti-inflammatory agent, a bone growth stimulating agent, a radiopaque agent, or an antioxidant.

In one embodiment, the compositions of the invention comprise one or more antimicrobial or antibiotics. Non-limiting examples of suitable antibiotics include broad spectrum antibiotics (e.g., gentamicin, clindamycin, crythromycin), gram-positive and gram-negative families of antibiotics (e.g., ampicillins and cephalosporins). In one embodiment, the composition also comprises agents such as TRICLOSAN, chlorohexidine, iodine, povidone iodine, colloidal silver, etc.

In one embodiment, the compositions of the invention comprise one or more local anesthetics or analgesics. Non-limiting examples include lidocaine, bupivacaine, tetracaine, and ropivacaine. Further examples include benzocaine and fentanyl (a potent non-opioid).

In one embodiment, the compositions of the invention comprise one or more anti-inflammatory agents such as non-specific ibuprofen and aspirin, or COX-2 specific inhibitors such as rofecoxib and celeboxib.

In one embodiment, the compositions of the invention comprise one or more antioxidants. Non-limiting examples of suitable antioxidants include IRGANOX 1010 and IRGANOX 1035 (Ciba Geigy), CYANOX 1790 and CYANOX 2777 (Cytec Industries), and vitamin F and vitamin E acetate (BASF Corp.). In certain embodiments, the antioxidant is present in an amount of from about 0.01% to 0.5% by weight of the composition.

In one embodiment, the compositions of the invention comprise one or more bone growth stimulating or osteoinductive agents such as peptide growth factors, bone morphogenetic proteins (BMP, e.g., rhBMP-2); demineralized bone matrix; transforming growth factors (TGF, e.g., TGF-(3); osteoblast cells, growth and differentiation factor (GDF), and combinations thereof. Further examples include other hone stimulatory organic agents including HMG-CoA reductase inhibitors, such as a member of the statin family, e.g., lovastatin, simvastatin, pravastatin, fluvastatin, atorvastatin, cerivastatin, mevastatin, and pharmaceutically acceptable salts, esters or lactones thereof. Additional embodiments include pyrrolidones, prostaglandins, vitamins, bis phosphonates, phospholipids and combinations of any of the foregoing.

Other Optional Components

The compositions of the invention may also comprise one or more optional component including, without limitation, those described herein. In one embodiment, a composition of the invention comprises one or more active agents. In one embodiment, the one or more active agent is selected from an antimicrobial agent, an anesthetic, an analgesic, an anti-inflammatory agent, an osteoconductive agent, and a chemotherapeutic agent. In one embodiment, a composition of the invention further comprises one or more of a softening agent, a chelating or sequestering agent (e.g., sodium gluconate, polyaspartic acid, and EDTA), and a filler or thickener. In one embodiment, a composition of the invention further comprises one or more of a radiotransparent agent, a radiopaque agent, an antioxidant, an anti-adhesion agent (e.g., hyaluronic acid), and a colorant (e.g., gentian violet, D&C Violet #2, and D&C Green #6). In certain embodiments, a composition of the invention may comprise a combination of arty of the foregoing.

Non-limiting examples of suitable antibiotics include broad spectrum antibiotics (e.g., gentamicin, clindamycin, erythromycin), gram-positive and gram-negative families of antibiotics (e.g., ampicillins and cephalosporins).

Non-limiting examples of suitable anesthetics or analgesics include lidocaine, bupivacaine, tetracaine, and ropivacaine. Further examples include benzocaine and fentanyl (a potent non-opioid).

Non-limiting examples of suitable anti-inflammatory substances include the non-specific drugs, ibuprofen and aspirin or the COX-2 specific inhibitors such as rofecoxib and celeboxib.

Non-limiting, examples of suitable osteoconductive agents for use as additives in the compositions of the invention include, for example, collagen, a calcium phosphate (such as hydroxyapatite, tricalcium phosphate, or fluorapatite), demineralized bone matrix, and combinations thereof.

Non-limiting examples of suitable antioxidants include IRGANOX 1010 and IRGANOX 1035 (Ciba Geigy), and CYANOX 1790 and CYANOX 2777 (Cytec Industries). In certain embodiments, the antioxidant is present in an amount of from about 0.01% to 0.5% by weight of the composition.

An additional softening component is sometimes required in order to make the monolithic solid more pliable. This is particularly required for compositions employing Poloxamers with molecular weights in excess of 500 kD (e.g., Pluronic F-127) and polyethyleneglycol based materials with molecular weights greater than 4000 kD. In preferred embodiments, the dispersion accelerant also serves as a softener. In any case, suitable softeners are often insoluble or low solubility liquid or paste emollients or surfactants (e.g., Pluronic L-123). Many preferred softeners arc insoluble or low solubility neutral surfactants with HLBs less than 40, preferably less than 30, more preferably less than 20. Most preferable surfactants for this use have HLBs less than 10 and include Pluronic L-121, L101, and L-123. Eastman SAIB, tocopherol and its derivatives may also be useful as softeners.

Optional fillers and thickeners for use as additives in the compositions of the invention include, for example, cholesterol, calcium carbonate, starch, modified starch, starch derivatives, mineral and vegetable oils (e.g., castor bean oil, sunflower oil, olive oil, and purified derivatives thereof), glycerol and glycerol derivatives, micro crystalline cellulose, gums, sorbitans and sorbitol derivatives.

Non-limiting examples of a radiotransparent substance include air, nitrogen gas, carbon dioxide, and oxygen gas. Non-limiting examples of a radiopaque substance include barium sulfate ($BaSO_4$), ceramic particles, bone, and zirconium dioxide ($ZrO2$). Examples of commercially available radiopaque substances include LIPIODOL, HYPAQUE, and OMNIPAQUE. At least one radiotransparent substance and/or radiopaque substance, when present, is present in the compositions in an amount of from about 0.1% to about 40% by weight of the composition, and, in embodiments, from about 0.1% to about 10% by weight of the composition.

Dissolution Assays

The compositions of the invention have enhanced durability in the surgical environment in part due to their decreased water solubility. The dissolution time of compositions is tested, for example, in an in vitro assay. In one such assay, the test composition is formed into a disk of uniform dimension and placed in a 37° C. water bath. The time to dissolution or dispersion is measured.

Beaker Dissolution Screening Method

In the results reported here for the Beaker dissolution screening method, samples were manually formed into a uniform disc, 14 mm wide and 3 mm thick. The discs were submerged into dissolution buffer by pressing them onto the side of a glass beaker containing 200 ml of phosphate buffer, pH 7.4, at 37° C. below the buffer surface. The submerged discs were observed every thirty minutes or until complete dissolution occurred and the time of dissolution was recorded.

Biopsy Bag Dissolution Screening Method

In a variant of the dissolution assay, the test composition is formed into a disk of uniform dimensions and its weight is recorded. The weight of a corresponding number of biopsy bags is also recorded. Disks are placed into biopsy bags, fitted with a weight and submerged into a buffered dissolution bath. At specific time points the submerged discs are retrieved, dried, and weighed to determine the weight of the formulation lost to dissolution.

In the examples reported herein, an equal amount of each sample was manually pressed into a uniform disc (14 mm wide and 3 mm thick), and placed into a biopsy bag (45×75 mm, 200 mesh, VWR catalog #29000-050) and briefly clipped into a potassium phosphate buffer solution (50 mM). The bag containing each sample was then blotted for 4 seconds and its weight recorded. The bags were secured with a dialysis bag closure device and placed into a potassium phosphate buffer solution bath at secured inside a biopsy bag and placed into a glass beaker containing ~400 ml of phosphate buffer, pH 7.4, at 37° C.

At the indicated time points, samples were removed from the bath and the dialysis closure released. The sample is blotted for 4 seconds and then weighed and the percentage of the sample remaining was calculated.

Wire Mesh Dissolution Screening Method

Another in vitro variant of the dissolution assay for which results are reported herein replaces the biopsy bag with a mesh cup for holding the test article. An equal amount of each sample was compacted into 60-mesh (250 micron) baskets (McMaster Carr Part #14416 FW 0.600), placed into beakers containing ~400 ml phosphate buffered saline, and maintained at 37° C. and agitated at ~20-25 rpm shaker speed. At the indicted time points the basket was removed from the bath, weighed wet, and air dried overnight and weighed again to determine dry weight. Dry weights are used to determine dissolution rates, and wet weights are used to determine the rate of water uptake.

In Vitro Hemostasis Model

The relative hemostatic efficacy of the compositions of the invention can be evaluated in vitro, for example, by the HEM test or a similar test. The HEM test evaluates both adherence to bone or similar material and solubility in the presence of water. If adherence is too weak or if the composition is too water-soluble, it will not provide an acceptable tamponade hemostasis. The HEM test mimics one of the most demanding situations for tamponade hemostasis in orthopedic practice—the pedicle screw hole. A pedicle screw hole is a hole drilled into spinal bone by the surgeon. It is often as large as 6 mm in diameter. In the context of the HEM test, the pedicle screw hole is mimicked by drilling a 6 mm hole (in some variations other diameter holes are employed which may be 2, 3, 4, or 5 mm) into a full-thickness section of central bovine tibia. A closed system is created by sealing the ends of the bone section with a resin. The resin accommodates tubing that shunts water into and out of the center of the bone. (i.e., where the marrow would be in the intramedullary canal). The composition to be tested is uniformly packed into the 6 mm hole and subjected to the shear force of water flowing through the center of the bone. The amount of time for which the composition is able to withstand the flow is measured, to a maximum time of 3600 seconds.

The compositions of the invention can also be evaluated for tamponade efficacy in vivo, for example, by its ability to produce hemostasis in living rabbit bone. In this test, a 4 mm hole is drilled through the cortices of the humerus into the intramedullary canal. Once active bleeding is confirmed, the test compound is applied to the defect. Each compound is applied at 4 or 5 different sites in different animals. Hemostasis is monitored in two ways. First, the time to hemostasis post-application is recorded. This is measured from the time of removal of excess material to the cessation of bleeding. Second, hemostasis efficacy is measured by recording whether or not hemostasis is maintained without significant re-bleeding or leakage for the duration of the experiment. In addition, the handling properties of each composition are evaluated by the surgeon. The surgical testers are asked to estimate the preparation time which includes any kneading, warming, or mixing time required prior to application. The testers are also asked to judge the ease of application as poor, fair, good, or excellent and to comment on the handling properties of the putty (pliability, stickiness). Preferably, the compositions of the invention stop the active bleeding within a few seconds or at least within 1 minute after application to the site and maintain hemostasis for at least 1 to 3 hours.

In certain embodiments, the hemostasis efficacy of the compositions is measured with an in vitro assay such as the HEM test described herein. Preferably, the compositions of the invention are able to maintain hemostasis in such an assay for at least 30 minutes at least 90 minutes, at least 12.0 minutes, or for from about, 30 to 60 minutes or 120 minutes, 90 to 120 minutes, 120 to 180 minutes, 180 to 240 minutes, or longer.

Tactile Proper

The compositions of the invention also have specific tactile properties. For example, the compositions of the invention have a suitable stiffness, spreadability, stickiness, and slipperiness. Stiffness is a measure of how rigid or fluid the composition is when manipulated by hand. This is important because for effective application to bleeding bone surfaces, the composition cannot be too rigid or too fluid. Preferably, the compositions of the invention have a "putty-like" consistency. This quality is evaluated by manually manipulating the sample with surgical gloved hands. Spreadability is a measure of how easily and uniformly the composition spreads over a bone surface so that all pores are evenly blocked. This is evaluated by spreading a 1 cm diameter sphere of the composition across a simulated bone (Sawbone) and measuring, in centimeters, the length of the track produced. Stickiness is a measure of cohesiveness on surgical gloved hands. This is evaluated by pressing a 1 cm diameter sphere of the composition between two gloved fingers and estimating the quantity of material sticking to the opposing finger. Slipperiness may also be evaluated using a similar test with the exception that the sphere is first submerged in a 37° C. water bath and then handled. All of these properties affect the ability of the composition to be used easily and effectively during surgery. These properties are preferably measured by a panel of from 4 to 10 evaluators who grade each of the three properties on a scale of 0 (best) to 5 (worst). Exemplary scales for each of the three properties are given in Table 1.

TABLE 1

| Grade | Stiffness | Spreadability (on model bone) | Stickiness (to latex gloves) |
|---|---|---|---|
| 0 | Putty | Excellent - Softest | No Adhesion |
| 1 | Paste | Good - Soft | Slight |
| 2 | Wax | Substantial | Moderate |
| 3 | Gel | Moderate | Substantial |
| 4 | Solid or Powder | Hard | Severe |
| 5 | Fluid | Hardest | Bonding to glove surface |

In many cases the slower solubilization time of the inventive putties leads to reduced slipperiness compared to a reference composition. Reduced slipperiness in aqueous environments offers improved surgical usefulness in handling and placement of the hemostatic putties. Slipperiness can also be reduced through incorporation of many of the described granular materials (e.g., particulate ceramics and glasses). In one embodiment, a composition of the invention has reduced slipperiness compared to a reference composition selected from OSTENE; a composition exemplified in U.S. Pat. Nos. 7,553,913 and 7,829,616 by Wellisz, et al., and a composition exemplified in U.S. Pat. No. 7,074,425 by Constantine, et al. In preferred embodiments, the slipperiness of a composition of the invention after exposure to water is at least 10% less than a reference composition.

Slipperiness can be determined empirically through the measurement of the coefficient of friction. Guidance for measurement of the coefficient of friction can be found in ASTM C-1028-07. A useful instrument of quantification is the pull-meter, commercially available from Gabrielli Technology (code GT0810 or GT0966). Preferably, the coefficient of friction is determined in both the wet and dry conditions using the Gabbrielli Pull-meter according to ASTM C 1028-07. In one embodiment, a composition of the invention has an increased coefficient of friction compared to a reference composition selected from OSTENE; a composition exemplified in U.S. Pat. Nos. 7,553,913 and 7,829,616 by Wellisz, et al., and a composition exemplified in U.S. Pat. No. 7,074,425 by Constantine, et al. In one embodiment, the coefficient of friction for a composition of the invention is at least about 10% higher than that of the reference composition.

The compositions of the invention have the consistency of a putty. Compositions having a suitable putty-like consistency are characterized by their stiffness or viscosity. In certain embodiments, the compositions of the invention have an improved stiffness compared to reference composition. In certain embodiments, the reference composition is selected from commercial bone hemostats such as BONE WAX, OSTENE, and HEMASORB. In other embodiments, the reference composition is selected from a composition exemplified in U.S. Pat. Nos. 7,553,913 and 7,829,616 by Wellisz, et al., and a composition exemplified in U.S. Pat. No. 7,074,425 by Constantine, et al. In one embodiment, a composition of the invention is less stiff than a reference composition selected from BONE WAX and OSTENE, a composition exemplified in U.S. Pat. Nos. 7,553,913 and 7,829,616 by Wellisz, et al., and a composition exemplified in U.S. Pat. No. 7,074,425 by Constantine, et al. In one embodiment, a composition of the invention has about the same stiffness as a reference composition selected from HEMASORB.

The relative stiffness or viscosity of a composition can be measured using techniques known in the art. In one example, stiffness is measured using a hand penetrometer. The putty is placed in a 13 by 3 mm cylindrical sample holder and a spatula is used to level and smooth the surface of the sample. The sample is maintained in the block for 1 minute at room temperature. A hard wax is prepared by removing from packaging and placing on a flat surface without pre-handling under the penetrometer tip. Samples are tested on a calibrated penetrometer with a 50 gram weight. Specifically, the 50 gram weight is placed on top of the plunger rod (the hole in the center of the weight centers the weight on the plunger rod) and the top and lower locking screws are loosened to lower the head of the penetrometer so that the tip of the cone just touches the surface of the sample. The penetrometer head is then secured in place with the locking screws. At time zero, the plunger is released and held for 5 seconds to lock it in place at the depth of penetration. The indicator rod is pushed so that it comes into contact with the top of the plunger. Other standard methods may be employed including, e.g., parallel plate viscometers.

EXAMPLES

Example 1: FWS Screening

Certain gel-forming additives have been found to be particularly effective dissolution retardants in the FWS-based compositions of the invention. In particular, sodium carboxymethylcellulose of low, medium and high viscosities such as CMC LV, CMC MV and CMC HV were found to significantly increase the dissolution time of the FWS-based compositions as assayed in the in vitro test described above. In contrast, neither chitosan, sodium alginate, gelatin, nor oxidized cellulose, added in the same proportion as CMC, increased the dissolution time of the composition. This finding is illustrated by the following examples.

Each of the following samples was prepared by melting the listed components while stirring followed by stirring the melt while it cooled to ambient temperature and solidified. When CMC was used in a particular formulation it was added to the melted components as a powder and the composition cooled with stirring to form a putty-like material. All samples were allowed to sit at least 24 hours at room temperature, prior to screening for dissolution properties by the Beaker Method.

TABLE 2

| # | Formulation Assayed by the Beaker Method | Dissolution time (min) |
|---|---|---|
| 1a | OSTENE | 105 |
| 1b | OSTENE/CMC (MV) - 77%/23% | 450 |
| 2a | PEG 1450/PEG 400 - 90%/10% | 30 |
| 2b | (PEG 1450/PEG 400)/CMC (MV) - 90.9% (81.8/9.1)/9.1% | 450 |
| 2c | (PEG 1450/PEG 400)/sodium alginate - 90.9% (81.8/9.1)/9.1% | 30 |
| 2d | (PEG 1450/PEG 400)/chitosan - 90.9% (81.8/9.1)/9.1% | 30 |
| 2e | (PEG 1450/PEG 400)/gelatin - 66% (90/10)/-33% | 30 |
| 2f | (PEG 1450/PEG 400)/oxidized cellulose - 90.9% (81.8/9.1)/-9.1% | 30 |
| 3a | PEG Stearate - 80%/PLU L-121 - 20% | 30 |
| 3b | PEG Stearate - 60%/CMC (MV) - 20%/PLU L-121 - 20% | 300 |
| 3c | PEG Stearate - 80%/PLU L-121 - 15%/TOC - 5% | 30 |
| 3d | PEG Stearate - 60%/CMC (MV) - 20%/PLU L-121 - 15%/TOC - 5% | 330 |
| 3e | PEG Stearate - 40%/CMC (MV) - 40%/PLU L-121 - 15%/TOC - 5% | 450 |
| 4a | PLU F-127 - 77%/PLU L-121 - 23% | 420 |
| 4b | PLU F-127/PLU L-121 - 64.5%/CMC (MV) - 32.3%/TOC - 3.2% | 390 |
| 5a | PLU F-68 - 77%/PLU L-61 - 23% | 60 |
| 5b | PLU F-68 - 55.6%/PLU L-61 - 11.1%/CMC (MV) - 33.3% | 420 |
| 5c | PLU F-68 - 67%/PLU L-61 - 23%/CMC (MV) - 10% | 210 |
| 5d | PLU F-68 - 67%/PLU L-61 - 23%/CMC (LV) - 10% | 180 |
| 5e | PLU F-68 - 76.92%/PLU L-61 - 18.46%/TOC - 4.62% | 90 |
| 5f | PLU F-68 - 38.46%/PLU L-121 - 18.46%/CMC (MV) - 38.46%/TOC - 4.62% | 430 |
| 5g | PLU F-68/PLU L-121 - 66.67%/CMC (MV) - 33.33% | 420 |
| 5h | PLU F-68/PLU L-121 - 66.67%/CMC (LV) - 33.33% | 180 |
| 5i | PLU F-68/PLU L-121 - 66.67%/CMC (HV) - 33.33% | Hard, not evaluated |
| 6a | PEG Stearate - 80%/PLU L-121 - 10%/Polypropyleneglycol 2000 - 10% | 30 |
| 6b | PLU P-123 - 67%/PLU F-127 - 33% | 200 |

Abbreviations:
PLU—Pluronic (BASF),
L—Liquid Pluronic,
F—Solid Pluronic;
CMC—sodium carboxymethylcellulose (Sigma Aldrich),
(HV)—High Viscosity,
(MV)—Medium Viscosity,
(LV)—Low Viscosity;
TOC—Tocopheryl Acetate (BASF);
PEG—Polyethylene Glycol (Spectrum);
PEG Stearate - polyethylene glycol stearate ester, i.e., Polyoxyl 40 Stearate (Myrj$^R$ 52 = Polyethylene Glycol (40) Monostearate, USP, NF) (Spectrum);
OSTENE (Ceremed, Inc., Lot # W1570906).

Screening of these formulations revealed the addition of CMC to formulations 1a, 2a, 3a, 5a, 5e resulted in significantly prolonged, dissolution times. It is not known why the addition of CMC has such a remarkable effect on the rate of dissolution of the composition. Without being hound by any particular theory, one explanation for why the inclusion of CMC retards dissolution is that the hydrogel formed by the addition of a CMC-containing sample to warm buffer encapsulates the putty components within a CMC hydrogel, retarding dissolution by forcing component diffusion through the surrounding hydrogel or, alternatively, by forming a concentration gradient within the hydrogel that retards dissolution. An alternative is that dissolution retardation may result from hydrogen bonding between the components and the CMC hydrogel. Yet another possible explanation is that dissolution retardation results from a phenomenon analogous to gel partition chromatography where molecules diffuse through a hydrogel as a function of their molecular weight. The latter may explain why higher molecular weight Pluronic mixtures, e.g., ~4000, (Sample 3) do not require CMC to extend dissolution time.

Example 2: FWS Dissolution Kinetics

Dissolution curves were determined either using the Biopsy bag or the mesh basket approach. The data for the formulations listed in Table 3 are presented in FIGS. 1-4. Using the Biopsy hag dissolution method the following formulations were used to generate the data presented in FIGS. 2 & 3.

TABLE 3

| # | Formulations | Dissolution Method | Extrapolated Time to complete Dissolution (mins) |
|---|---|---|---|
| 7a | Ostene | BB | 60 |
| 7b | PEG reference: PEG 1450 - 90%/ PEG 400 - 10% | BB | 10 |
| 8a | PLU F-127 - 60%/PLU L-121 - 30%/HA/TCP - 10% | BB | >300 |
| 8b | PLU P-123 - 67%/PLU F-127 - 33% | BB | >300 |
| 8c | PLU F-127 - 77%/PLU L-121 - 23% | BB | 180 |
| 8d | PEG Stearate - 75%/CMC(MV) - 5%/ PLU L-121 - 10%/ Polypropyleneglycol 2000 - 10% | BB | 240 |
| 9a | PEG4K - 70%/PLU P-123 - 30% | BB | >300 |
| 9b | PLU F-127 - 77%/PLU L-121 - 23% | BB | 180 |
| 9c | PEG Stearate - 75%/PLU L-121 - 20%/CMC - 5% | BB | >100 |
| 10 | PEG Stearate - 35%/CMC(MV) - 5%/ PLU L-121 - 5%/ TOC - 5%/HA/βTCP - 50% | MB | 360* |

Example 3: FWS Water Uptake and Dissolution

The Effect of Incorporating CMC and Gamma Irradiation (Irradiation Dose)

The effect of CMC on the rate of water uptake in a putty with or without exposure to gamma irradiation was evaluated using the following formulations. Results are presented in Tables 4-6 and in FIG. 3.

TABLE 4

| # | Formulation: Mesh Basket Method | Extrapolated Time to complete Dissolution (mins) |
|---|---|---|
| 11a | PEG Stearate - 74%/CMC (HV) - 6%/ PLU L-121 - 10%/Polypropylene glycol 2000 - 10% | 600 |
| 11b | PEG Stearate - 80%/PLU L-121 - 10%/ Polypropylene glycol 2000 - 10% | 240 |

TABLE 5

| | Water Uptake @ 0.5 hrs | Water Uptake @ 1 hrs | Water Uptake @ 5 hrs |
|---|---|---|---|
| WSH (no gamma) | 30% | 43% | 79% |
| WSH (no CMC) | 0 | 0 | 0 |
| WSH (gamma) | 17% | 46% | 65% |

TABLE 6

| | % Mass loss @ 0.5 hrs | % Mass loss @ 1 hrs | % Mass loss @ 3 hrs | % Mass loss @ 5 hrs |
|---|---|---|---|---|
| WSH (no gamma) | 18 | 32 | | 77 |
| WSH (no CMC) | | 25 | 75 | 100* |
| WSH (gamma) | 16 | 32 | | 72 |

*fully dissolved at 4 hours

The effect of the incorporation of particulate calcium phosphate was evaluated using the mesh basket method for the formulations in Table 7. Results of the evaluation of the formulations listed in Table 7 are presented in Table 8.

TABLE 7

| # | Formulation | Expected Dissolution Time (mins) |
|---|---|---|
| 12a | PEG Stearate - 75%/CMC - 5%/PLU L-121 - 10%/ Polypropylene glycol 2000 - 10% | 600 |
| 12b | PEG Stearate - 35%/CMC (MV) - 5%/PLU L-121 - 5%/TOC - 5%/HA/β-TCP - 50% | 360* |

*/HA/β-TCP component will persist for weeks

TABLE 8

| hrs | mean % water up take X (SD) | mean % mass loss X (SD) |
|---|---|---|
| 1 | 31.4 (1.2) | 19.2 (1.5) |
| 3 | 50.0 (3.7) | 38.4 (3.5) |
| 6 | 61.8 (1.6) | 62.2 (2.9) |

Example 4

Figure 1B:
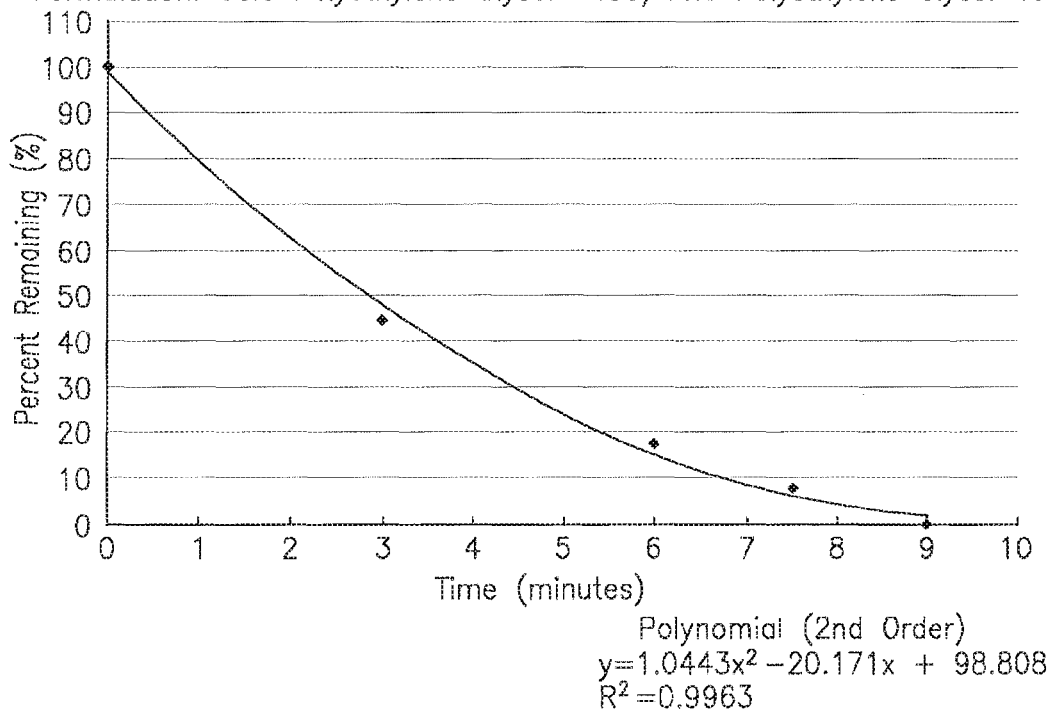
Figure 2A:
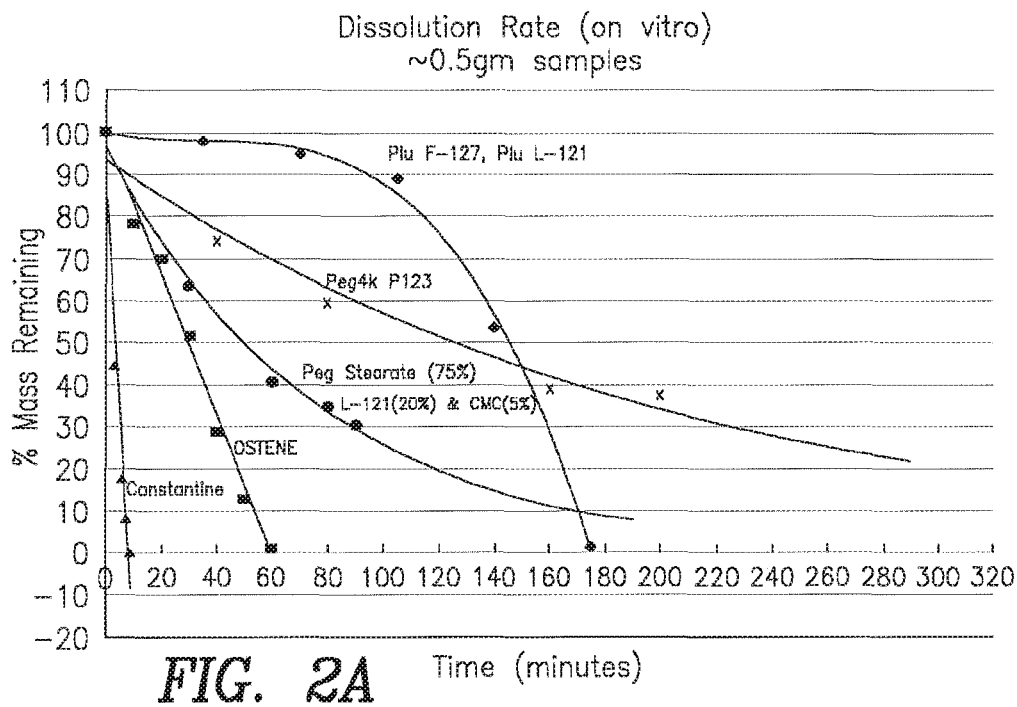
FIGS. 2A-B: (A) A graph of the dissolution kinetics of representative inventive compositions compared to the two reference materials in FIG. 1 (Ostene & PEG1450/400) All formulations exceed the dissolution time of the reference materials. (B) A graph of the dissolution kinetics of addition of the inventive compositions. Dissolution was analysed by the biopsy bag method. (see specification for method details).
Figure 2B:
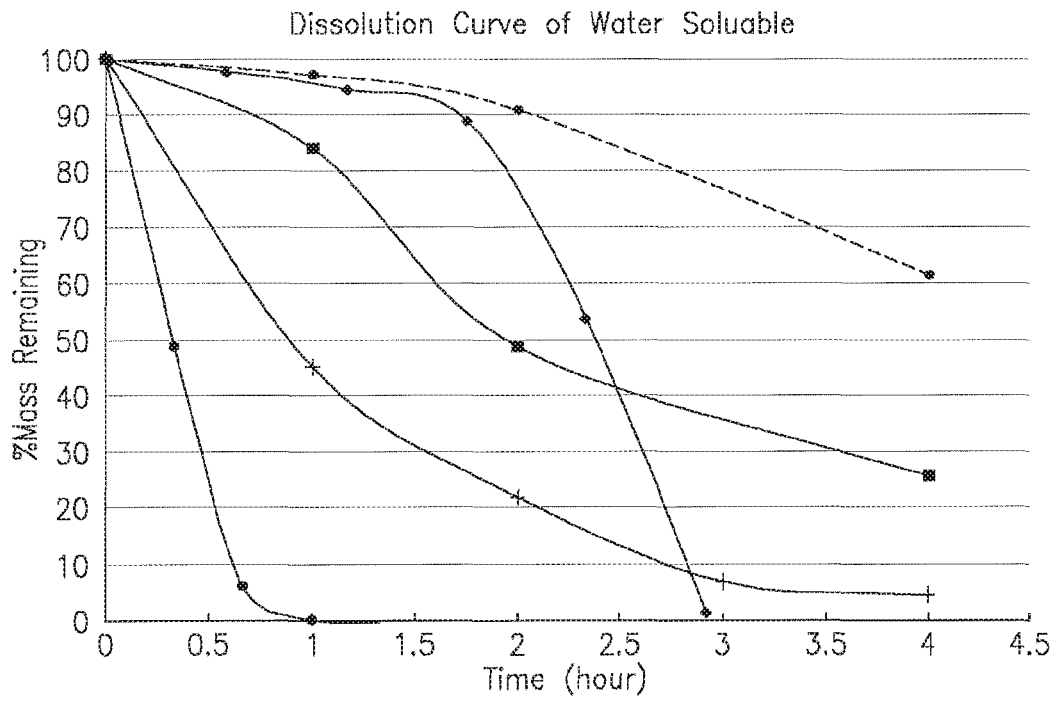

Use of high molecular weight polyethylene glycols to produce longer dissolution time putties. These PEGS are provided has hard waxy powders. To produce a putty they were melted in the presence of Pluronic P123, a Vaseline-like wax. The melt was cooled with continuous mixing to produce a formable putty. Dissolution rates were determined after 24 hours. Each of these materials underwent complete dissolution over a time period 5 to 40 times longer than the reference materials (FIG. 1 A-B). The results are presented in Table 9.

TABLE 9

| # | Formulation | Time to Complete Dissolution (min) |
|---|---|---|
| 13a | Peg 4k - 70%/PLU P-123 - 30% | 300 |
| 13b | Peg 6k - 70%/PLU P-123 - 30% | 400 |

TABLE 9-continued

| # | Formulation | Time to Complete Dissolution (min) |
|---|---|---|
| 13c | Peg 8k - 70%/PLU P-123 - 30% | 400 |
| 13d | Peg 10k - 70%/PLU P-123 - 30% | 400 |

Example 5: PWS-Based Compositions

Compositions were prepared as described above and tested for dispersal time, since these materials do not completely dissolve. Since these samples were prepared from less soluble components, dispersion was evaluated every 24 hours. The formulations listed in Table 10 were tested.

TABLE 10

| Sample | Components | Observations after 24 hr at 37 C. Beaker test | Handling |
|---|---|---|---|
| 14 | 62.5% SMS/27.5% L-121/10% F-68 | intact | good |
| 15 | 52.5% SMS/27.5% L-121/20% F-68 | intact | good |
| 16 | 42.5% SMS/27.5% L-121/30% F-68 | partially disintegrated | good |
| 17 | 32.5% SMS/27.5% L-121/40% F-68 | partially disintegrated | good |
| 18 | 40% CS/20% TCPμm/35% L-121/5% TA | intact | good |
| 19 | 42.5% GMS/27.5% L-121/30% F-68 | partially disintegrated | good |
| 20 | 67.5% SMS/27.5% L-121/5% P-123 | intact | good |

Abbreviations:
SMS—Sorbitan Monostearate;
L-121—Pluronic L-121;
F-68—Pluronic F-68;
TCPμm—Tricalcium Phosphate (micronized);
CS—Calcium Stearate;
TA—Tocopheryl Acetate;
GMS—Glycerol Monostearate.

These data indicate that formulations 16, 17 & 19 disperse well and are expected to clear well in vivo.

Additional formulations were prepared, which are listed in Table 11.

TABLE 11

| | Beaker test | minutes |
|---|---|---|
| 21 | CHOL - 55%/PLU P-123 - 45% | 200 |

Other Formulations

Other useful formulations for the preparation of PWS hemostatic compositions are listed in Table 12.

TABLE 12

| # | Components | Comment |
|---|---|---|
| 22 | 60% SMS/40% L-121 | Forms well, somewhat sticky |
| 23 | 70% SMS/30% L-121 | Forms well, somewhat sticky after cooling and handling |
| 24 | 75% SMS/25% L-121 | Crumbly after cooling |
| 25 | 67.5% SMS/32.5% L-121 | Very good formation/handling; some SMS reformed after cooling |
| 26 | 67.5% SMS/27.5% L-121/5% P-123 | Forms, handles well |
| 27 | 60% GMS/30% L-35/10% TA | Forms well, but sticky |
| 28 | 67.5% GMS/22.5% L-35/10% TA | Slightly gritty/sticky |
| 29 | 50% GMS/30% L-121/20% PEG 1500 | Good handling and forms well; becomes tacky after continued manipulation |
| 30 | 50% GMS/30% L-121/20% PEG 2000 | No stickiness after prolonged manipulation; does become a 'rock' after sitting out |
| 31 | 45% GMS/45% IPM/10% PEG-stearate | Good putties dispersed after 24 hrs @ 37 degrees |
| 32 | 40% GMS/20% IPM/20% PEG stearate 20% PLU 121 | Good putties dispersed after 24 hrs @ 37 degrees |
| 33 | 60% PEG 1500/20% L-121/20% GMS | Forms and handles well; leaves a little residue after prolonged manipulation |
| 34 | 42.5% Bonewax/27.5% L-121/30% F-68 | |
| 35 | 42.5% Bonewax/27.5% GMC/30% F-68 | |
| 36 | 42.5% GMS/27.5% glycerol mono caprylate/30% F-68 | |
| 37 | 30% hypromellose/42.5% SMS/27.5% L-121 | |

Abbreviations:
SMS—sorbitan monostearate;
L-121—Pluronic L-121;
F-68—Pluronic F-68;
TCPμm—tricalcium phosphate (micronized);
CS—calcium stearate;
TA—tocopheryl acetate;
GMS—glycerol monostearate;
GMC—glycerol mono caprylate.

Example 6: In Vivo HEMOSTASIS

Various formulations were tested for their hemostatic efficacy in surgically created defects in the distal femur of New Zealand White (NZW) rabbits. 4 mm diameter holes were drilled in surgically exposed lateral and medial cortices of the epicondyles. Active bleeding was confirmed at each defect site prior to the application of the hemostatic materials. The test articles were then kneaded to the desired consistency if necessary, and applied to the bleeding defect to establish hemostasis. In all examples hemostasis was achieved immediately upon placement of the putty.

TABLE 13

| | Formulations for in vivo hemostasis | Range of Hemostasis Time (in-vivo) (mins) |
|---|---|---|
| | FWS Formulations | |
| 38a | PEG Stearate - 75%/CMC (MV) - 5%/PLU L-121 - 15%/TOC - 5% | <5 |
| 38b | PEG4K - 70%/PLU P-123 - 30% | <15 |
| 38c | PEG Stearate - 75%/PLU L-121 - 20%/CMC - 5% | <15 |
| 38d | PEG Stearate - 75%/CMC - 5%/PLU L-121 - 10%/Polypropylene glycol 2000 - 10% | >15 |
| 38e | PEG Stearate - 35%/CMC (MV) - 5%/PLU L-121 - 5%/TOC - 5%/HA/β-TCP - 50% | >30 |
| 38f | PEG Stearate - 35%/CMC (MV) - 5%/PLU L-121 - 10%/Polypropylene glycol 2000 - 10%/HA/β-TCP - 40% | >60 |
| 38g | PLU F-127 - 60%/PLU L-121 - 30%/HA/β-TCP - 10% | >60 |
| 38h | PLU F-127 - 60%/PLU P-123 - 40% | <90 |
| | PWS Formulation | |
| 38i | PLU P-123 - 45%/CHOL - 55% | >60 |

Example 7

A rabbit bone implantation study was conducted to evaluate the in vivo absorption of WSH-1.

The study involved New Zealand White Rabbits with defect sites located in the right and left femur diaphyses, measuring approximately 3 mm in diameter and full thickness in depth. At the desired endpoints animals were sacrificed and the implant sites were excised for histopathology. The tissue explants were fixed, decalcified and embedded in paraffin prior to sectioning and staining with hematoxylin and eosin. The presence of residual implant material was defined as the actual observation of material or voids where material had washed out during processing. The amount of material was assessed using the following scoring system:

0=No test article present (no residual material)
1=Trace amounts left; ~¼ or less residual material remaining (25% or less)
2=Small amount; ~½ or less residual material remaining (less than 50%)
3=Large amount; more than ½ residual material remaining (more than 50% to 100%)

The test article was substantially absorbed by 8 days.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A hand-moldable hemostatic composition having the consistency of a putty, wherein the composition is effective for tamponade hemostasis of a bone or cartilage comprising:
   a. a water-soluble ethoxylated fatty acid;
   b. a freely water soluble (FWS) non-particulate solid base material comprising: i) block copolymers of ethylene and propylene oxide and ii) polypropylene glycol, wherein the composition further comprises a particulate material embedded within the FWS solid base material; and
   c. a water absorbing dissolution retardant in an amount effective to increase the dissolution time of the FWS nonparticulate solid base material, wherein the water absorbing dissolution retardant is a carboxymethyl cellulose, or a sodium, potassium or lithium salt thereof, and wherein the carboxymethyl cellulose is present in an amount that is 5-15% by weight of the putty, thereby increasing the dissolution time of the FWS non-particulate solid base material, and
   wherein the composition has sufficient strength to adhere directly to the moist surfaces of bleeding bone or cartilage, thereby creating a static interface that allows blood clotting to occur.

2. The composition of claim 1, wherein the particulate material is absorbable, nonabsorbale, resorbable, or a mixture thereof.

3. The composition of claim 2, wherein the absorbable material comprises a particulate ceramic or glass material.

4. The composition of claim 3, wherein the particulate ceramic or glass material is selected from the group consisting of substituted calcium phosphates; glass; calcium sulfate; calcium phosphosilicate; sodium phosphate; calcium aluminate; bone or a bone substitute; calcium phosphate; tricalcium phosphate; tetracalcium phosphate; dicalcium phosphate; calcium pyrophosphate; hydroxyapatite; biphasic calcium phosphates; hydroxyapatite and TCP containing calcium phosphates; multiphasic calcium phosphates; highly porous nanocrystalline hydroxyapatite (HA) in the presence of nanoporous silica ($SiO_2$); glass-ionomer, absorbable phosphate glass; an osteoconductive plastic, polymer or polyurethane; and combinations thereof.

5. The composition of claim 4, wherein the substituted calcium phosphates comprise a silica, strontium or magnesium calcium salt substitution.

6. The composition of claim 4, wherein the glass is a bioglass.

7. The composition of claim 1, wherein the composition further comprises a tocopherol acetate.

8. The composition of claim 1, wherein the composition further comprises one or more agents selected from the group consisting of an antimicrobial agent, an anesthetic, an analgesic, an antioxidant, a bone growth stimulating agent, an anti-inflammatory agent, an osteoconductive agent, an osteoconductive component, a peptide growth factor, a chemotherapeutic agent, a softening agent, a chelating or sequestering agent, a radiotransparent agent, a radiopaque agent, and an anti-adhesion agent.

* * * * *